United States Patent
Easley et al.

(10) Patent No.: US 11,826,033 B2
(45) Date of Patent: Nov. 28, 2023

(54) ILLUMINATED SCLERAL DEPRESSOR ASSEMBLY

(71) Applicant: XRV-IP, LLC, St. Charles, MO (US)

(72) Inventors: James C. Easley, Cottleville, MO (US); Matthew LaConte, Chesterfield, MO (US)

(73) Assignee: XRV-IP, LLC, St. Charles, MO (US)

( * ) Notice: Subject to any disclaimer, the term of this patent is extended or adjusted under 35 U.S.C. 154(b) by 0 days.

(21) Appl. No.: 17/932,490

(22) Filed: Sep. 15, 2022

(65) Prior Publication Data
US 2023/0084104 A1 Mar. 16, 2023

Related U.S. Application Data

(60) Provisional application No. 63/244,945, filed on Sep. 16, 2021.

(51) Int. Cl.
*A61B 17/02* (2006.01)
*A61B 90/30* (2016.01)

(52) U.S. Cl.
CPC .... *A61B 17/0231* (2013.01); *A61B 2090/306* (2016.02)

(58) Field of Classification Search
CPC ....................... A61B 17/0231; A61B 2090/306
USPC ................ 600/236, 245, 246, 247, 248, 249
See application file for complete search history.

(56) References Cited

U.S. PATENT DOCUMENTS

| | | | |
|---|---|---|---|
| 11,471,242 B1 * | 10/2022 | Diao | A61F 9/007 |
| 2005/0171408 A1 * | 8/2005 | Parker | A61B 17/0293 |
| | | | 600/249 |
| 2008/0081952 A1 | 4/2008 | Josephberg | |
| 2012/0283523 A1 * | 11/2012 | Yadlowsky | A61F 9/00763 |
| | | | 600/249 |
| 2016/0062041 A1 | 3/2016 | Lee et al. | |
| 2017/0128133 A1 | 5/2017 | Pinnow | |
| 2017/0238919 A1 * | 8/2017 | Foxman | A61B 17/0231 |
| 2019/0240506 A1 * | 8/2019 | Finger | A61B 1/07 |

(Continued)

FOREIGN PATENT DOCUMENTS

| | | |
|---|---|---|
| CN | 210354653 U | 4/2020 |
| KR | 10-2017-009451 A | 1/2017 |

OTHER PUBLICATIONS

International Search Report and Written Opinion for PCT/US2022/076477, dated Jan. 2, 2023, 10 pages.

*Primary Examiner* — Eduardo C Robert
*Assistant Examiner* — David C Comstock
(74) *Attorney, Agent, or Firm* — Armstrong Teasdale LLP (57) ABSTRACT

A scleral depressor assembly includes a scleral depressor, an optical fiber, and a reflector. The scleral depressor includes an elongate body and a head disposed at a distal end of the elongate body. The scleral depressor defines an internal lumen extending through the elongate body and terminating within the head. The optical fiber is disposed within the lumen and includes a distal end positioned within the head. The optical fiber distal end includes a beveled end face that is obliquely oriented with respect to a central axis of the internal lumen. The reflector is disposed at the distal end of the optical fiber and is configured to reflect light emitted from the optical fiber distal end along a light path out of the scleral depressor head in a direction that is approximately orthogonal to the central axis of the internal lumen.

21 Claims, 9 Drawing Sheets

(56) References Cited

U.S. PATENT DOCUMENTS

2020/0360104 A1   11/2020  Kehren-Quitsdorf et al.
2021/0220077 A1*  7/2021  Bacher ................... A61B 90/30

* cited by examiner

ILLUMINATED SCLERAL DEPRESSOR ASSEMBLY

CROSS-REFERENCE TO RELATED APPLICATIONS

This application claims priority to U.S. Provisional Patent Application No. 63/244,945, filed Sep. 16, 2021, the disclosure of which is hereby incorporated by reference in its entirety.

BACKGROUND

The field of the disclosure relates generally to medical devices, and more specifically, to medical devices used in ophthalmology.

A standard technique in ophthalmic procedures is depression of the sclera to visualize the periphery of the retina. Visualization of the upper periphery can be used during inspection of retinal dislocation, tears, subretinal fluid, abnormal anatomy, or to locate areas for vitreous shaving. Typically, a skilled assistant is needed to assist with either illuminating the eye or depressing the sclera, making the procedure difficult if an assistant is unavailable.

At least some known devices include an endoilluminator device that is inserted into a transparent or translucent cap to illuminate the eye through the sclera, eliminating the need for an assistant to provide the illumination of the eye during the procedure. Current limitations of existing devices are low illumination intensity, which limits visualization of geometry within the eye; the direction of the limiting amount of light axially back towards the posterior pole; and the necessity of an endoilluminator to be inserted into the device to provide the illumination.

BRIEF DESCRIPTION

In one aspect, a scleral depressor assembly includes a scleral depressor, an optical fiber, and a reflector. The scleral depressor includes an elongate body and a head disposed at a distal end of the elongate body. The scleral depressor defines an internal lumen extending through the elongate body and terminating within the head. The optical fiber is disposed within the lumen and includes a distal end positioned within the head. The optical fiber distal end includes a beveled end face that is obliquely oriented with respect to a central axis of the internal lumen. The reflector is disposed at the distal end of the optical fiber and is configured to reflect light emitted from the optical fiber distal end along a light path out of the scleral depressor head in a direction that is approximately orthogonal to the central axis of the internal lumen.

In another aspect, an illuminated scleral depressor assembly includes a scleral depressor, a light source, an optical fiber, and a reflector. The scleral depressor includes an elongate body and a head disposed at a distal end of the elongate body. The scleral depressor defines an internal lumen extending through the elongate body and terminating within the head. The optical fiber is disposed within the lumen and extends between the light source and the scleral depressor. The optical fiber comprises a distal end positioned within the head and including a beveled end face that is obliquely oriented with respect to a central axis of the internal lumen. The reflector is disposed at the distal end of the optical fiber and is configured to reflect light emitted from the optical fiber distal end along a light path out of the scleral depressor head in a direction that is approximately orthogonal to the central axis of the internal lumen.

In yet another aspect, a method of assembling a scleral depressor assembly includes providing a scleral depressor that includes an elongate body and a head disposed at a distal end of the elongate body, where the scleral depressor defines an internal lumen extending through the elongate body and terminating within the head. The method further includes providing an optical fiber that is disposed within the lumen and includes a distal end positioned within the head, where the distal end includes a beveled end face that is obliquely oriented with respect to a central axis of the internal lumen. The method further includes providing a reflector disposed at the distal end of the optical fiber, and coupling the optical fiber to a light source such that light emitted by the light source is transmitted through the optical fiber and reflected by the reflector along a light path out of the scleral depressor head in a direction that is approximately orthogonal to the central axis of the internal lumen.

Although specific features of various embodiments may be shown in some drawings and not in others, this is for convenience only. Any feature of any drawing may be referenced and/or claimed in combination with any feature of any other drawing.

DETAILED DESCRIPTION

The present disclosure is directed to ophthalmologic surgical instruments, and more specifically, to illuminated scleral depressor assemblies. Embodiments of the illuminated scleral depressor assemblies described herein include a scleral depressor having an elongate body and a head disposed at a distal end of the body. The scleral depressor defines an internal lumen that extends through the elongate body and terminates within the head portion. The assembly also includes an optical fiber disposed within the lumen and including a distal end positioned within the head. The distal end includes a beveled end face that is obliquely oriented with respect to a central axis of the internal lumen. In some embodiments, the assembly also includes a light source that can be coupled to the optical fiber to transmit light therethrough. The assembly also includes a reflector disposed at the distal end of the optical fiber and configured to reflect light emitted from the optical fiber distal end along a light path out of the scleral depressor head in a direction that is approximately orthogonal to the central axis of the internal lumen. The reflector reflects the emitted light from the optical fiber, while the optical fiber distal end allows the reflective surface of the reflector to be positioned in close proximity to the optical fiber, thereby facilitating reducing the required diameter of the reflector as compared to other known assemblies.

The examples described herein include an ophthalmologic surgical instrument including one or more integrated optical fibers that supply a high amount of light to be transmitted out of the tip of the instrument and subsequently through the sclera. The inclusion of an optical fiber within the device can eliminate the need to use a separate endoilluminator. Embodiments of the illuminated scleral depressor assemblies described herein can improve usability and illumination intensity by integrating a larger optical fiber into the depressor and directing the illumination in a non-axial direction. The features that direct the illumination radially allow a user to aim the illumination back towards the pupil to minimize the pathway the light takes from the instrument to the user and therefore minimize loss.

In some embodiments, the ophthalmologic surgical instrument or device includes a transparent distal head, with geometries used for scleral depression, a rigid shaft, a handpiece, and one or more optical fibers used for transmitting light through the instrument and out of the transparent head. The distal face of the optical path is beveled to allow non-axial transmission of the illumination aided by a reflective surface bonded to the beveled face. The device is suitable for illumination through the sclera during ophthalmic procedures such as peripheral vitreous shaving. The non-axial illumination improves the illumination by directing it towards the pupil and, therefore, toward the user.

In some embodiments of the present disclosure, the medical device includes an ophthalmologic device, an optometric device, a probe, a vitrectomy device, a microsurgical device, an endoscopic surgical device, a neurosurgical device, or a plastic surgical device. In some embodiments, the medical device is used an as instrument, such as a microsurgical instrument, in an operation (e.g., surgery) conducted in or around an eye. The device is used, for example, in surgical treatment of retinal diseases, as for example resulting from hypertonia, or other vascular changes.

Figure 1:
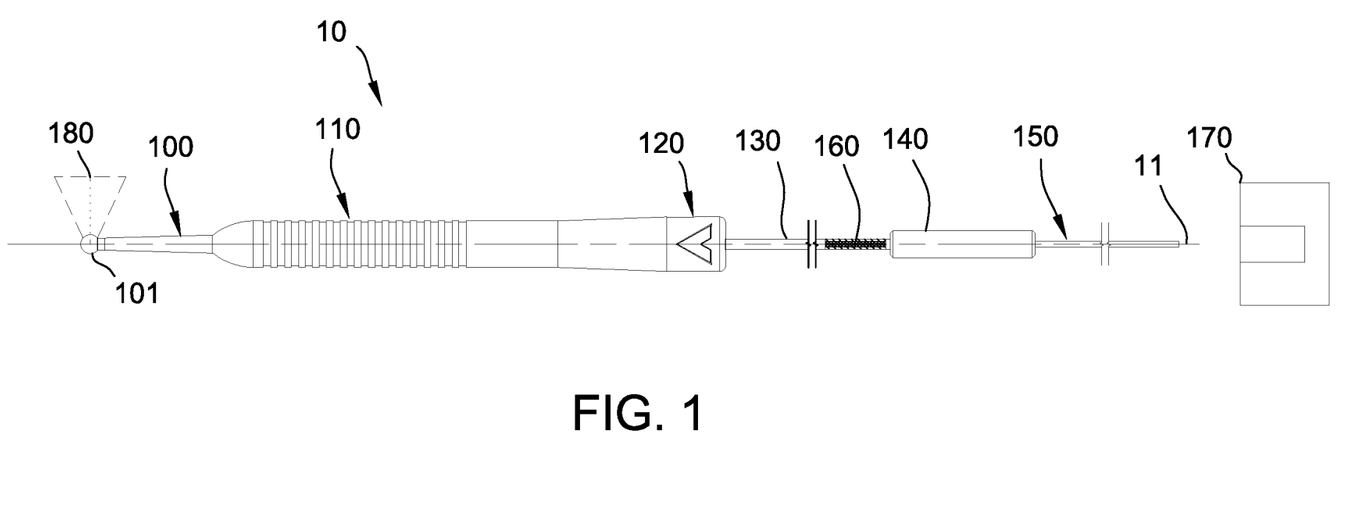
FIG. 1 is a side view of an exemplary illuminated scleral depressor assembly.

FIG. 1 is a side view of an exemplary illuminated scleral depressor assembly 10. In the illustrated embodiment, the scleral depressor assembly 10 includes a scleral depressor 100, a handle 110, a cap 120, a sheath 130, a fiber handle 140, an illumination adaptor 150, an optical fiber 160, and an illumination source 170. The scleral depressor assembly 10 extends along a central longitudinal axis 11, which is coaxial with respective central longitudinal axes of the other components of the scleral depressor assembly 10 in the illustrated embodiment (e.g., the scleral depressor 100, the handle 110, the cap 120, the sheath 130, the fiber handle 140, the illumination adaptor 150, and the optical fiber 160). In use, the illuminated scleral depressor assembly 10 is used to illuminate portions of the eye and/or to depress the sclera. For example, a user of the scleral depressor assembly 10 (e.g., a surgeon) can grasp the fiber handle 140 and insert or otherwise optically couple the illumination adaptor 150 to the illumination source 170. The illumination source 170 produces light that enters the optical fiber 160, which is protected by the sheath 130. The light is transmitted by the optical fiber 160 through the handle 110 to the head 101 of the scleral depressor 100, and is directed out of the head 101 via a reflector, as described in further detail herein. The emitted light 180 is directed out of the head 101 in a direction approximately orthogonal to the central axis 11 of the scleral depressor assembly 100, as shown in FIG. 1. As used herein, the term "approximately orthogonal" refers to a direction that is within ±30° of the orthogonal direction. By way of example, light that is emitted out of the head 101 in a direction approximately orthogonal to the central axis 11 is emitted along or about a central axis (e.g., central axis 182, shown in FIG. 6) that is within ±30 degrees of an orthogonal or perpendicular line to the central axis 11. In some embodiments, the emitted light 180 may be emitted in a direction that is substantially orthogonal to the central axis 11 (e.g., within ±10° of the orthogonal direction). In other embodiments, the emitted light 180 may be emitted in a direction other than approximately orthogonal to the central axis 11 (e.g., beyond ±30 degrees of the orthogonal direction).

The light source 170 may be any suitable light source that enables the illuminated scleral depressor assembly 10 to function as described herein. Examples of light sources suitable for use with the illuminated scleral depressor assembly 10 include, for example and without limitation, arc lamps, light emitting diodes (LEDs), incandescent-based light sources designed for illuminating optical fibers, light sources included in commercially available vitrectomy surgery machines (e.g., the Alcon Constellation Vision System, the Bausch and Lomb Stellaris PC, DORC Eva surgical systems), and combinations thereof.

Figure 2:
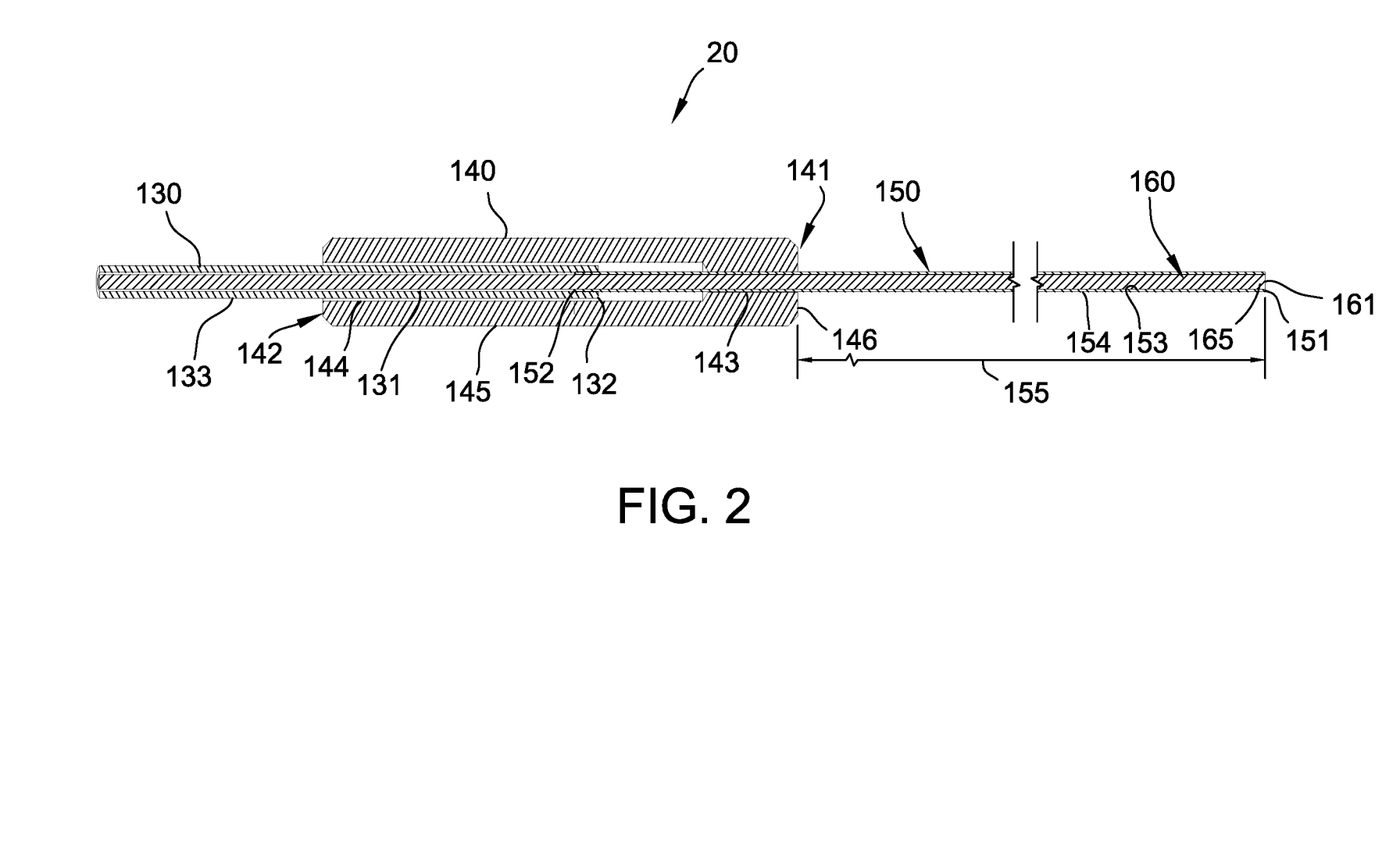
FIG. 2 is a cross-sectional view of a proximal portion of the illuminated scleral depressor assembly shown in FIG. 1.

FIG. 2 is a cross-sectional view of a proximal end portion 20 of the illuminated scleral depressor assembly 10 shown in FIG. 1. As shown in FIG. 2, the illumination adaptor 150 includes a generally tubular structure that extends from a proximal end 151 to a distal end 152. The illumination adaptor 150 can be constructed of stainless steel or any other suitable rigid material capable of withstanding the thermal load of the illumination source 170. The illumination adaptor 150 defines a lumen 153 that is sized and shaped to receive the optical fiber 160 therein. For example, the lumen 153 has a diameter suitable for insertion and affixing of a proximal end 165 of optical fiber 160. In one example, the lumen 153 has a diameter in the range of is 0.011 inches (in.) (0.28 millimeters (mm)) to 0.050 in (1.27 mm). The optical fiber proximal end 165 can be coupled to the illumination adaptor 150 using any suitable coupling or affixing means that enables the illuminated scleral depressor assembly 10 to function as described herein. Suitable examples include, for example and without limitation, adhesive, press-fit, crimp, or other mechanical methods.

Figure 5:
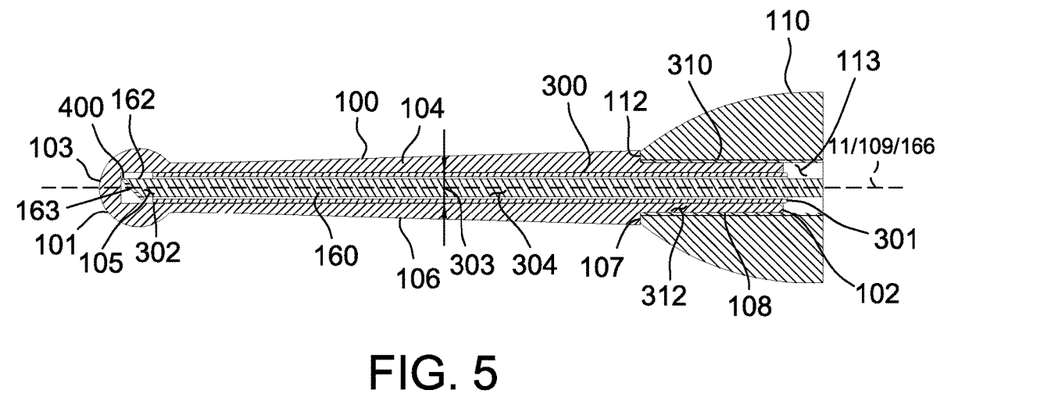
FIG. 5 is a cross-sectional view of a distal portion of the illuminated scleral depressor assembly shown in FIG. 1.
Figure 6:
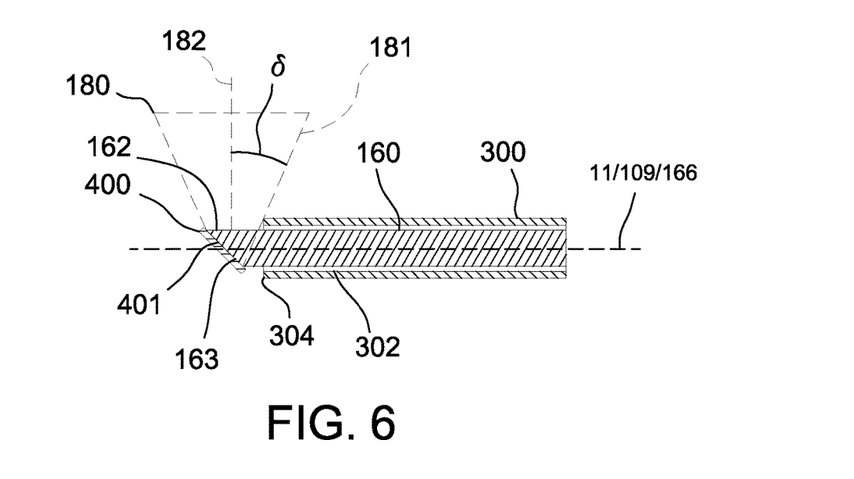
FIG. 6 is an enlarged view of the distal portion of the illuminated scleral depressor assembly shown in FIG. 5.
Figure 7:
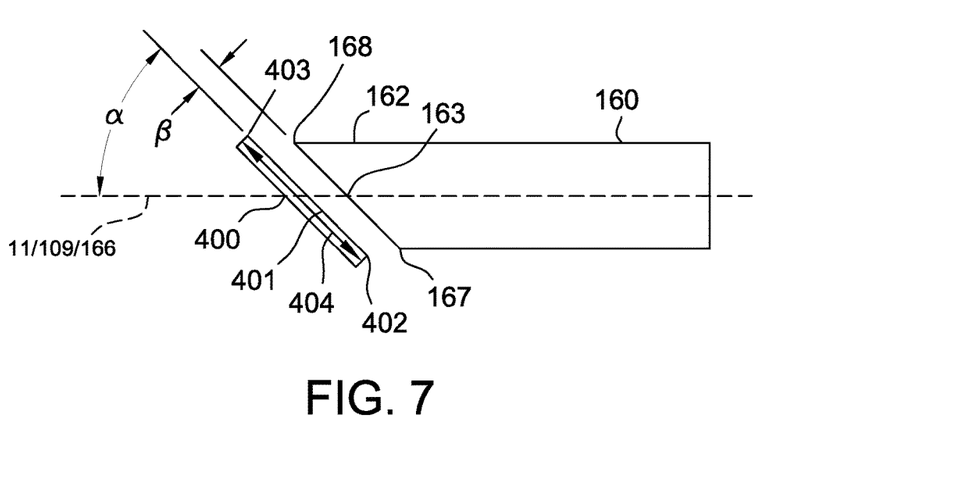
FIG. 7 is a further enlarged view of the distal portion of the illuminated scleral depressor assembly shown in FIG. 6.

The optical fiber 160 extends from the proximal end 165 to a distal end 162 (shown in FIGS. 5-7). The proximal end 165 includes a proximal end face 161 which, in the illustrated embodiment, is planar and is coupled approximately flush (i.e., coterminous) with the proximal end 151 of the illumination adaptor 150. The optical fiber proximal face 161 can be polished or cleaved to create a surface with minimal or reduced imperfections to mitigate heat accumulation and optimize the amount of light entering the optical fiber 160.

The optical fiber 160 can have any suitable construction that enables the illuminated scleral depressor assembly 10 to function as described herein. In the illustrated embodiment, the optical fiber 160 is a single fiber constructed of polymethylmethacrylate (PMMA), a plastic with a numeric aperture within a range of 0.25 to 0.75. In other embodiments, the optical fiber 160 can be constructed of any material suitable for transmission of light, including, for example and without limitation, glass. Additionally, in some embodiments, the optical fiber 160 is constructed of multiple fibers such that there is a junction within the optical path (see, e.g., FIG. 8). In another embodiment, the optical fiber 160 may be an endoillumination device that is inserted within the scleral depressor 100. In yet another embodiment the scleral depressor 100 could be a separate device that is installed onto or within the path of the optical fiber 160.

In the illustrated embodiment, the proximal end 151 of the illumination adaptor 150 and the proximal end face 161 of the optical fiber 160 are inserted into the illumination source 170 to couple the optical fiber 160 to the illumination source 170. More specifically, the illumination adaptor 150 is coupled to the illumination source 170 by inserting a length or segment 155 of the illumination adaptor 150 into the illumination source 170. In the illustrated embodiment, the insertion segment 155 extends from the optical fiber proximal face 161 to a proximal face 146 of the fiber handle 140. The length and outer geometry of the illumination adaptor insertion segment 155 can be selected based on the specific illumination source 170 used in the illuminated scleral depressor assembly 10. Examples of suitable dimensions of the illumination adaptor insertion segment 155 include a diameter, measured at an outer surface 154 of the illumination adaptor, in the range of 0.035 in (0.89 mm) to 0.375 in (9.53 mm) and a length, measured from the optical fiber proximal face 161 to the fiber handle proximal face 146, in the range of 0.25 in (6.35 mm) to 4.00 in (101.6 mm).

As shown in FIG. 2, the optical fiber 160 of the illustrated embodiment has a constant diameter along its entire length. In other embodiments, the diameter of the optical fiber 160 can be manipulated to change the characteristics of the light entering the optical fiber 160 to optimize the use of the light exiting the illumination source 170. In some embodiments, for example, a diameter of the optical fiber 160 along its proximal end 165 may be enlarged relative to the distal end to create a funnel-like feature. The optical fiber 160 can have any suitable diameter that enables the illuminated scleral depressor assembly 10 to function as described herein. As one example, the diameter of the optical fiber 160 can be in the range of 0.25 mm to 1.0 mm.

The fiber handle 140 extends from a proximal end 141 defining the proximal face 146 to a distal end 142, and defines a proximal lumen 143 and a distal lumen 144. The proximal lumen 143 extends distally from the proximal end 141, and the distal lumen 144 extends proximally from the distal end 142 to the proximal lumen 143. In the illustrated embodiment, the proximal lumen 143 and the distal lumen 144 have different diameters, although in other embodiments the proximal lumen 143 and the distal lumen 144 may have the same diameter. In the illustrated embodiment, the fiber handle 140 facilitates handling and manipulation of the optical fiber 160 and related components. For example, the illumination adaptor distal end 152 is affixed within the fiber handle proximal lumen 143 for assisting with insertion of the illumination adaptor 150 into the illumination source 170. Additionally, the fiber handle distal lumen 144 is sized and shaped to receive a proximal end 132 of the sheath 130 therein such that the sheath 130 can be affixed to the fiber handle 140.

The fiber handle 140 can be constructed of, for example and without limitation, plastic or any other suitable material that enables the illuminated scleral depression assembly 10 to function as described herein. The diameter of the fiber handle 140, measured along an outer surface 145 of the fiber handle, can be selected to facilitate ergonomic handling by the user. In some embodiments, for example, the diameter of the fiber handle 140 is in the range of 0.063 in (1.60 mm) to 0.375 in (9.53 mm). The fiber handle 140 can be omitted from the illuminated scleral depression assembly 10 in some embodiments.

The sheath 130 has a generally tubular construction and defines an inner lumen 131 sized and shaped to receive a portion of the optical fiber 160 therein. The sheath inner lumen 131 is sufficiently large to insert the optical fiber 160 therein, and an outer diameter of the sheath, measured along an outer surface 133 of the sheath 130, is sized such that the material is adequately flexible. The sheath 130 in this embodiment is constructed of a flexible polyvinyl chloride (PVC) plastic, but any suitable tubular material for a medical device sheath with sufficient flexibility may be used. The sheath 130 can be coupled or affixed to the optical fiber 160 using any suitable techniques that enable the illuminated scleral depressor assembly 10 to function as described herein. Suitable examples include, for example and without limitation, coextrusion and over-molding.

Figure 3:
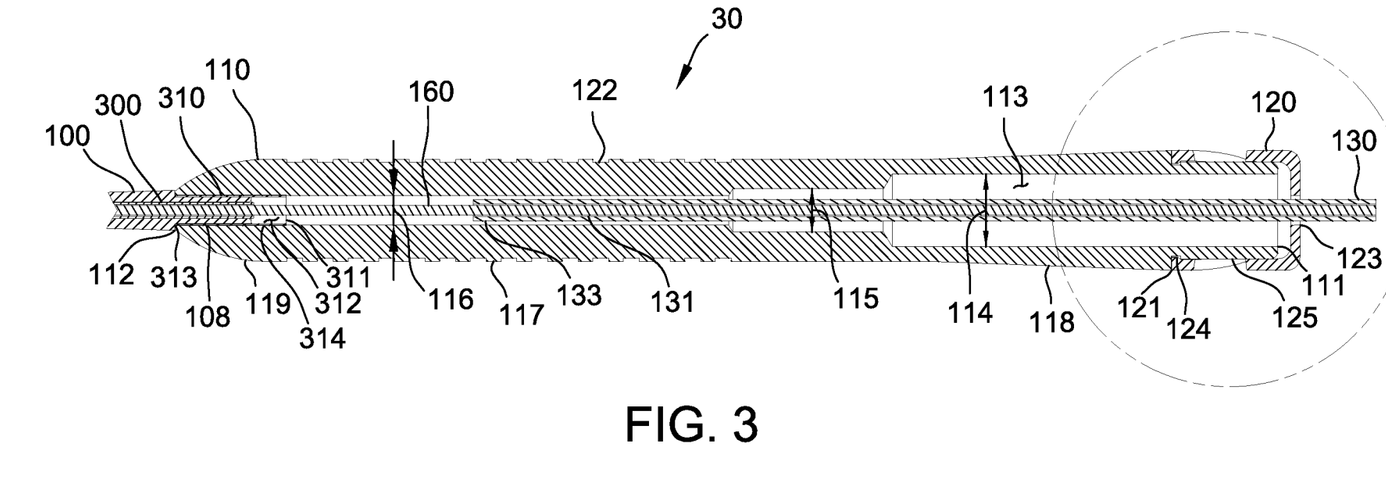
FIG. 3 a cross-sectional view of a handle portion of the illuminated scleral depressor assembly shown in FIG. 1.
Figure 4:
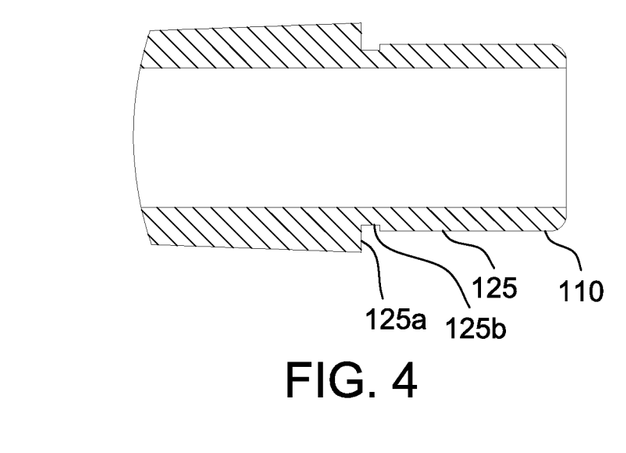
FIG. 4 is an enlarged view of the handle portion shown in FIG. 3.

FIG. 3 is cross-sectional view of a handle portion 30 of the illuminated scleral depressor assembly 10 shown in FIG. 1, and FIG. 4 is an enlarged cross-sectional view of a portion of the handle 110 of the illuminated scleral depressor assembly 10. As shown in FIGS. 3 and 4, the handle 110 extends from a proximal end 111 to a distal end 112, and defines an inner lumen 113 having a series of stepped internal diameters 114, 115, and 116 as the lumen 113 extends from the handle proximal end 111 to the handle distal end 112. The illustrated handle inner lumen 113 includes a proximal lumen diameter 114, an intermediate lumen diameter 115, and a distal lumen diameter 116. The internal lumen diameters 114, 115, and 116 of this embodiment are sized to allow for the optical fiber 160 and the sheath 130 to enter or be inserted into the inner lumen 113 of the handle 110. Additionally, the distal lumen diameter 116 of this embodiment is sized to allow for connection (e.g., via a press fit) of a reduction bushing 310 to facilitate connection of the scleral depressor 100 to the handle 110, as described further herein.

The handle 110 of this embodiment is generally cylindrical and is constructed of a plastic suitable for medical devices. Examples of suitable plastics include, for example and without limitation, acrylonitrile butadiene styrene (ABS) and acetal resin.

The illustrated handle 110 also includes a grip 117, a proximal taper 118, a distal taper 119, and a proximal step 125. The grip 117 is configured to facilitate gripping and manipulation of the illuminated scleral depressor assembly 10, and may include any suitable textured or gripping features that enable the handle 110 to function as described herein, including for example and without limitation grooves (e.g., radial or axial), knurls, dimples, over-molded viscoelastic materials, or any other features that increase friction for a user while manipulating the handle 110. The grip 117 in this embodiment includes a series of radial grooves 122. The handle 110 has a suitable diameter along the grip 117 and overall length to allow for ergonomic manipulation by the user without interfering with surrounding equipment or anatomy. In some embodiments, for example, the handle 110 has a diameter along the grip 117 within the range of 0.125 in (3.18 mm) to 0.50 in (12.7 mm), and an overall length within the range of 2.00 in (5.08 centimeters (cm) to 4.5 in (11.43 cm).

The distal taper 119 reduces the diameter at the handle distal end 112 to improve visualization of the eye during the scleral depression procedure. The proximal taper 118 in this embodiment increases the diameter of the handle 110 to match that of the cap 120. As shown in FIG. 4, the proximal taper 118 ends at a shoulder 125a of the proximal step 125, which transitions into a retention groove 125b and then to the proximal step 125, which ends at the handle proximal face 111.

The cap 120 is retained on the handle 110 by inserting the proximal end 111 of the handle 110 into a cavity defined by the cap 120 until a distal face 121 of the cap 120 contacts or engages the proximal step shoulder 125a. In this embodiment, the cap 120 includes a retention detent 124 that is received within the retention groove 125b to retain the cap 120 on the handle 110. Additionally, the cap 120 includes a cap access hole 123 sized and shaped to receive the optical fiber 160 and the sheath 130 therethrough. The cap 120 can be constructed of any suitable materials that enables the illuminated scleral depressor assembly 10 to function as described herein including, for example and without limitation, molded thermoplastic, such as ABS or polypropylene.

The reduction bushing 310 is a tubular component that may be constructed of, for example and without limitation, stainless steel or any other suitable material that enables the illuminated scleral depressor assembly 10 to function as described herein. The reduction bushing 310 includes a reduction bushing proximal face 311, a reduction bushing outer surface 314, a reduction bushing lumen 312, and a reduction bushing distal face 313. The reduction bushing 310 can also be affixed to the handle 110, such that the reduction bushing distal face 313 is flush with the handle distal end 112, using adhesives, over-molding, heat staking, threads, or any other method that retains the reduction bushing 310 relative to the handle 110. The reduction bushing lumen 312 is sized to accept a reduced diameter proximal end portion 108 of the scleral depressor 100, also referred to as scleral depressor proximal step 108.

FIGS. 5-7 illustrate additional internal details if the scleral depressor 100 and the scleral depressor head 101.

The scleral depressor 100 of the illustrated embodiment extends from a proximal end 102 to a distal end 103, and includes an elongate body 104 and the scleral depressor head 101 disposed at a distal end of the elongate body 104. The scleral depressor 100 defines an internal lumen 105 that extends from the proximal end 102 through the elongate body 104 and terminates within the scleral depressor head 101. In some embodiments, the internal lumen 105 contains an optically transparent fluid including, for example and without limitation, saline. The scleral depressor 100 also includes a tapered region 106 that tapers radially outward from the scleral depressor head 101 to a scleral depressor proximal shoulder 107, which transitions into the reduced diameter proximal end portion 108. In other embodiments, the tapered region 106 may be omitted and the scleral depressor 100 may have a constant diameter between the scleral depressor shoulder 107 and the scleral depressor head 101.

The scleral depressor 100 is connected to the handle 110 by the scleral depressor proximal step 108. In the illustrated embodiment, for example, the scleral depressor proximal step 108 is sized and shaped to be inserted within the reduction bushing lumen 312, with the scleral depressor proximal shoulder 107 in contact with the handle distal end 112, and is affixed to the reduction bushing 310 using, for example and without limitation, adhesives, a press-fit connection, one or more fasteners (e.g., setscrews), over-molding, or any suitable method to fix the position of the scleral depressor 100 relative to the handle 110. In other embodiments, the scleral depressor proximal step 108 can be inserted directly into the distal portion of the handle lumen 113.

In the illustrated embodiment, the scleral depressor 100 is constructed of transparent material such as, for example and without limitation, acrylic, polycarbonate, silica (i.e., glass), combinations thereof, or any other transparent material suitable for medical devices. Alternatively, one or more portions of the scleral depressor 100 can be constructed of non- or semi-transparent material, such as portions of the scleral depressor other than the scleral depressor head 101 within the region of emitted light 180.

The illustrated illuminated scleral depressor assembly 10 also includes a stiffening bushing 300 disposed within the scleral depressor lumen 105 radially between the scleral depressor 100 and the optical fiber 160. The stiffening bushing 300 is a tubular element constructed from stainless steel or any other suitable opaque material. The stiffening bushing 300 extends from a proximal end 301 to a distal end 302, and has an outer diameter 303 smaller than the distal lumen diameter 116 (FIG. 3). The stiffening bushing 300 defines a lumen 304 having a diameter larger than the diameter of the optical fiber 160. The stiffening bushing 300 can be coupled or affixed to the scleral depressor 100 using, for example and without limitation, adhesive, over-molding, heat staking, or any other suitable method. In the illustrated embodiment, the distal end 302 of the stiffening bushing 300 is positioned within the scleral depressor head 101 to shield the user from light emitted from the optical fiber 160 proximal to the scleral depressor head 101.

The optical fiber 160 is disposed within the lumen 105. A portion of the optical fiber 160 extends distally beyond the stiffening bushing 300 to define an exposed segment, which includes the distal end 162 of the optical fiber 160 and a reflector 400. As shown in FIGS. 5 and 6, the distal end 162 of the optical fiber 160 and the reflector 400 are positioned within the scleral depressor head 101. As shown in FIG. 6, the distal end 162 includes a beveled end face 163 that is obliquely oriented with respect to the central axis 11 of the scleral depressor assembly 10 and a central axis 109 of the scleral depressor lumen 105, which is coaxial with the central axis 11 of the scleral depressor assembly 10. The reflector 400 is operable to reflect light transmitted through the optical fiber 160, and the beveled end face 163 facilitates positioning a reflective surface 401 of the reflector 400 closer to the optical fiber 160 and thereby reducing or minimizing the required size or diameter of the reflector 400.

The reflector 400 is disposed at the distal end 162 of the optical fiber 160 and is oriented at an oblique angle α approximately equal to the bevel angle of the beveled end face 163. The reflector 400 is configured to reflect light emitted from the optical fiber distal end 162 along a light path 180 out of the scleral depressor head 101 in a direction that is approximately orthogonal to the central axis 109 of the internal lumen 105. That is, the beveled end face 163 and the reflector 400 are configured to divert light transmitted through the optical fiber 160 and emit the light 180 approximately orthogonal to the central axes 11 and 109. More specifically, light emitted from the reflector 400 forms an illumination pattern 181 that is emitted along or about a central axis 182. In the illustrated embodiment, the illumination pattern 181 is a conical illumination pattern, and the central axis 182 of the illumination pattern 181 is perpendicular to the central axes 11 and 109. In some embodiments, the illumination pattern 181 extends or spans an angle δ from the central axis 182. In some embodiments, the angle δ is within a range of approximately 10° to approximately 30° from the central axis 182. The illustrated illumination pattern 181 of reflected light 180 represents the range of the light output for the example embodiment. Because light travels down the optical fiber 160 at various angles with respect to the fiber axis, a number of light rays impinge on the reflector 400 at angles other than the orientation of the reflector 400 (45° in the illustrated embodiment), resulting in a radially expanding or conical illumination pattern 181.

FIG. 7 is an enlarged view of the distal end of illuminated scleral depressor assembly 10, showing the relative positions of the reflector 400 and the beveled end face 163 with respect to the central axis 11 and a central longitudinal axis 166 of the optical fiber 160. The reflector 400 is shown spaced from the beveled end face 163 in FIG. 7 for illustrative purposes. When assembled, the reflector 400 is positioned adjacent or in contact with the beveled end face 163. As shown in FIG. 7, the reflector 400 includes a reflective surface 401 that faces or is oriented towards the optical fiber 160. The reflective surface 401 is positioned on or adjacent the beveled end face 163 of the optical fiber 160 to reflect light emitted therethrough.

The reflector 400 and the reflective surface 401 are positioned at an angle α relative to the central axes 11 and 166. In some embodiments, the angle α is within the range of 30° to 60°. Such an orientation results in an output pattern central axis 182 (FIG. 6) that is oriented in the range of 60° to 120° relative to the central axes 11 and 109. The beveled end face 163 is positioned at an angle β relative to the reflective surface 401. In the illustrated embodiment, the beveled end face 163 is parallel to the reflective surface 401 (i.e., the angle β is 0°). In other embodiments, the angle β may be in the range of 0° to 15° degrees. Stated another way, the beveled end face 163 can be oriented at an oblique angle of between 15° to 75° relative to the longitudinal axis 166 of the optical fiber 160, and more suitably, between 30° to 60° relative to the longitudinal axis 166 of the optical fiber 160.

As shown in FIG. 7, the configuration and orientation of the beveled end face 163 results in the beveled end face 163 extending from a proximal edge 167 to a distal edge 168. Similarly, the reflector 400, specifically the reflective surface 401, extends from a proximal edge 402 to a distal edge 403.

In the illustrated configuration, the reflector proximal edge 402 is positioned proximally to the optical fiber bevel distal edge 168. In other words, the combination of the beveled end face 163 and the angled reflector 400 allows the reflector 400 to be positioned closer to the fiber distal end 162. As a result, the reflector 400 can be made smaller or more compact than it otherwise would need to be to capture the fiber's full output if the fiber distal face were flat or planar (i.e., not beveled). In the illustrated embodiment, for example, the optical fiber 160 and the reflector 400 extend the same radial distance from the central axes 11 and 166 such that the optical fiber 160 and the reflector 400 are the same size when viewed longitudinally from the distal end 162. As another example, a major dimension 404 of the reflective surface 401 (e.g., a diameter or width) can be less than 3 times larger than the diameter of the optical fiber 160.

The reflector 400 and, more specifically, the reflective surface 401 are positioned substantially adjacent to the beveled end face 163 and connected with no significant difference in the index of refraction. In the illustrated embodiment, the reflector 400 is formed as a disk that abuts the beveled end face 163 of the optical fiber 160. In other embodiments, the reflector 400 and reflective surface 401 can be implemented as a deposition or coating, such as a vapor deposition material or other coating, applied directly to the beveled end face 163. The reflector 400 and, more specifically, the reflective surface 401 are suitably constructed or made of optically reflective materials, including, for example and without limitation, aluminum, silver, steel, or alloys thereof.

Figure 8:
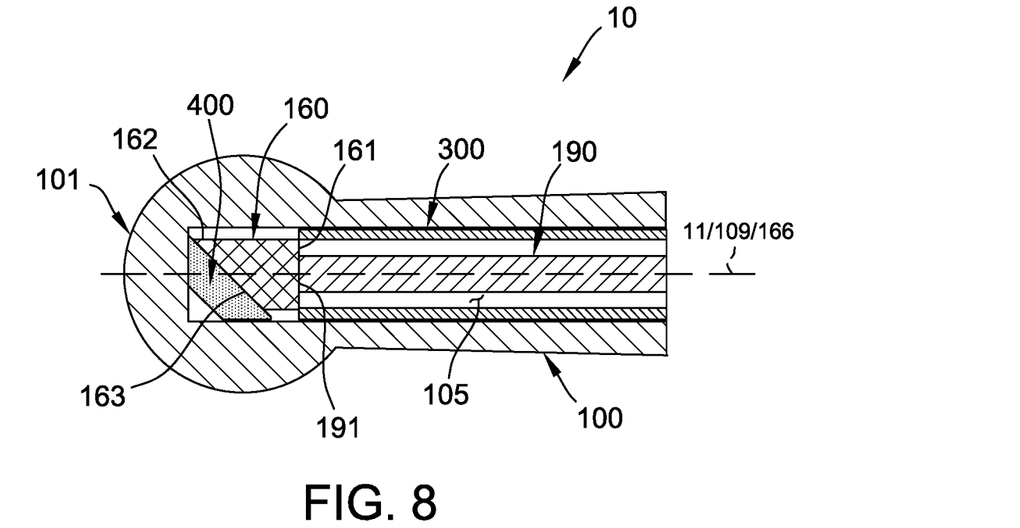
FIG. 8 is a cross-sectional view of a distal portion of the illuminated scleral depressor assembly of FIG. 1 including an alternative optical fiber assembly.

As noted above, the optical fiber 160 of the illustrated embodiment is a single fiber. In other embodiments, the optical fiber 160 can be constructed of multiple fibers such that there is a junction within the optical path. FIG. 8, for example, illustrates the illuminated scleral depressor assembly 10 including an optical fiber assembly that includes a first optical fiber 160 and a second optical fiber 190. As shown in FIG. 8, the first optical fiber 160 extends from the planar proximal end 161 (also referred to as an "input face") to the distal end 162 that includes the beveled end face 163 coupled to the reflector 400. The second optical fiber 190 includes a planar distal end 191 (also referred to as an "output face") that abuts with the proximal end 161 of the first optical fiber 160 to transmit light though the first and second optical fibers 160 and 190. The second optical fiber 190 can be constructed of the same materials as the first optical fiber 160 including, for example and without limitation, PMMA and glass. In some embodiments, the second optical fiber 190 is removable from the illuminated scleral depressor assembly 10. That is, the scleral depressor lumen 105 is adapted to removably receive the second optical fiber 190. For example, the second optical fiber 190 can be the optical fiber of a commercially available endoilluminator that, when used with the illuminated scleral depressor assembly 10, produces an illumination pattern that is emitted in a direction that is approximately orthogonal to the central axis 109 of the internal lumen 105. In other embodiments, the second optical fiber 190 can be a dedicated stand-alone fiber. In the illustrated embodiment, the proximal end 161 of the first optical fiber 160 can be located anywhere between the reflector 400 and the illumination source 170 (e.g., within the scleral depressor lumen 105). In the illustrated embodiment, the proximal end 161 of the first optical fiber 160 is disposed within the scleral depressor head 101.

Referring again to FIG. 5, the scleral depressor head 101 of the example embodiment is spherically shaped with a radius sized to allow for sufficient indentation of a patient's eye wall while being able to comfortably access the patient's orbit. For example, the radius of the scleral depressor head 101 can be in the range of 0.5 mm to 3 mm. Additionally, the surface finish of the scleral depressor head 101 in the example embodiment is smooth.

Figure 9:
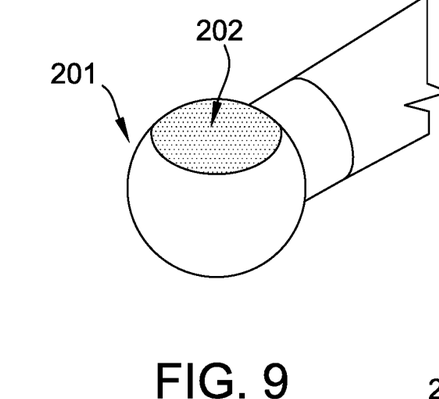
FIG. 9 is a perspective view of an alternative scleral depressor head suitable for use with the illuminated scleral depressor assembly of FIG. 1.
Figure 10:
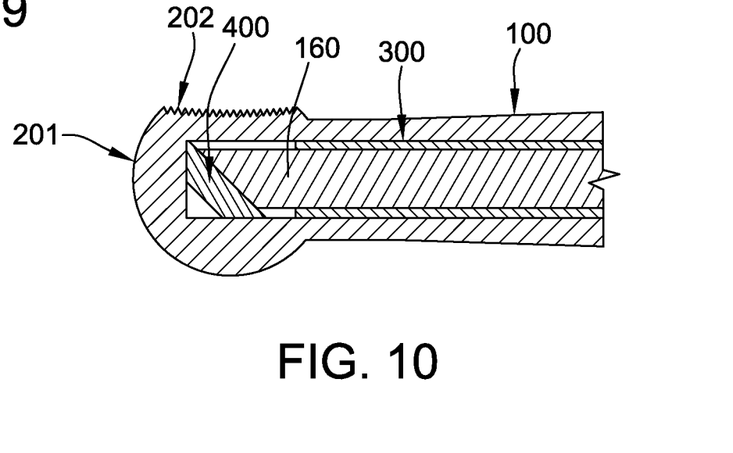
FIG. 10 is a cross-sectional view of the alternative scleral depressor head of FIG. 9 connected to the illuminated scleral depressor assembly of FIG. 1.

In other embodiments, the scleral depressor head 101 can be textured and/or include surface features to increase friction on the sclera or alter the emitted light 180 from the illuminated scleral depressor assembly 10. As illustrated in FIGS. 9 and 10, for example, an alternative scleral depressor head 201 includes a concave engagement surface 202 to assist in manipulating the eye, for example, during transillumination. The concave engagement surface 202 is positioned within the light path traversed by light reflected by the reflector 400, and has a suitable concave radius to facilitate maximizing the contact surface area and friction between the head 201 and the tissue. In some embodiments, for example, the concave engagement surface has a radius approximately matching the curvature of the eye (e.g., 0.50 inches or 12.7 mm). The concave engagement surface 202 can also be textured and/or include surface features, such as raised ribs or protrusions, to increase the coefficient of friction between the head 201 and the tissue and thereby decrease the force needed to manipulate the anatomy. The head 201 and concave engagement surface 202 are particularly suitable for use with trans-illumination to assist in visualization of anatomical features, and can be in combination with or in place of scleral depression.

Figure 11:
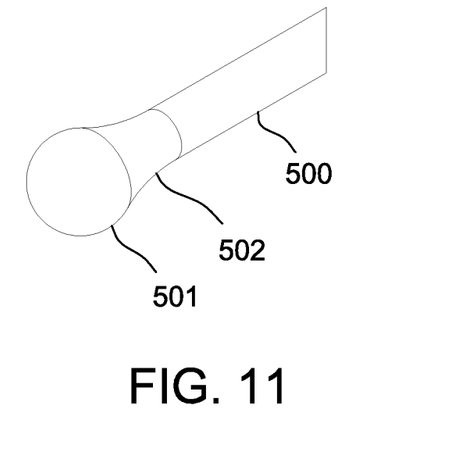
FIG. 11 is a perspective view of an example embodiment of a scleral depressor head geometry suitable for use with the illuminated scleral depressor of FIG. 1.
Figure 12:
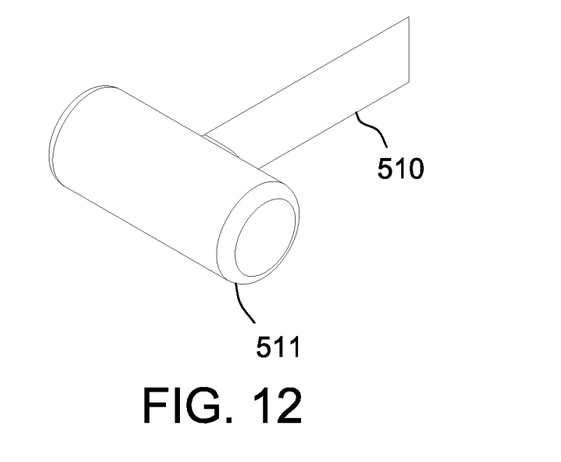
FIG. 12 is a perspective view of another example embodiment of a scleral depressor head geometry suitable for use with the illuminated scleral depressor of FIG. 1.
Figure 13:
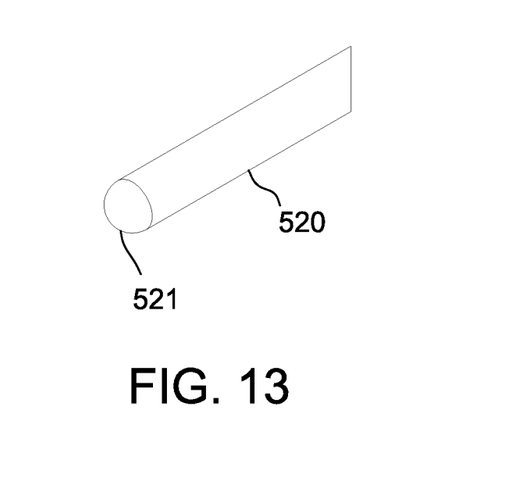
FIG. 13 is a perspective view of yet another example embodiment of a scleral depressor head geometry suitable for use with the illuminated scleral depressor of FIG. 1.

FIGS. 11-13 illustrate additional examples of suitable shapes and geometries scleral depressor heads that are suitable for use with the illuminated scleral depressor assembly 10 and the scleral depressor 100. Features of the head 201 and the concave engagement surface 202 shown and described with reference to FIGS. 9-10 can be implemented with any of the geometries illustrated in FIGS. 11-13. FIG. 11 illustrates a tear-drop geometry that includes a tear drop shaft 500, a tear drop shoulder 502, and a tear drop head 501. FIG. 12 illustrates a Schocket geometry that includes a Schocket shaft 510 and a cylindrical Schocket head 511. FIG. 13 illustrates a bullet geometry that includes a bullet shaft 520 and a bullet head 521. The scleral depressor heads shown and described herein can be manufactured from a variety of suitable materials, including for example and without limitation, acrylic, polycarbonate, glass, stainless steel, titanium, combinations thereof, or other suitable rigid materials commonly used for medical instruments. In embodiments where the scleral depressor head is constructed of an opaque or non-transparent material, the scleral depressor head may include a window (e.g., an opening or an area made of transparent material) to allow light reflected by the reflector to be emitted from the scleral depressor head.

Figure 14:
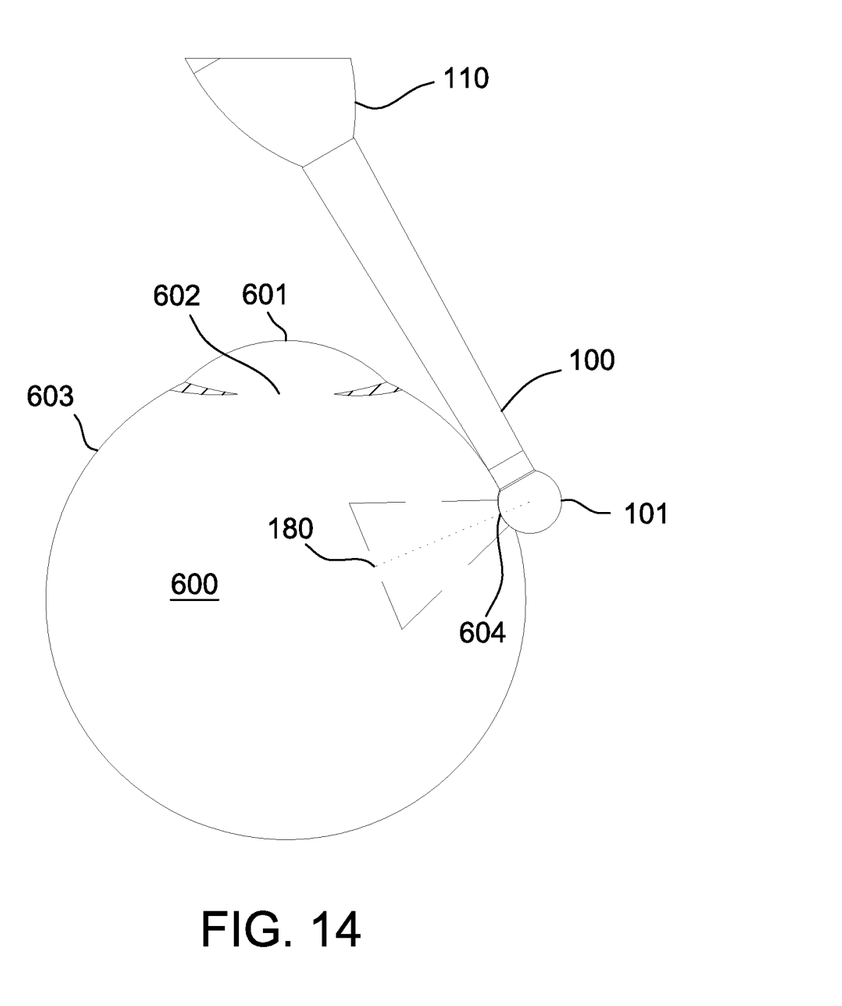
FIG. 14 is a schematic diagram illustrating an exemplary use of the illuminated scleral depressor assembly of FIG. 1.

FIG. 14 illustrates an exemplary use of the illuminated scleral depressor assembly 10 to provide illumination during a scleral depression procedure on a patient's eye 600. As shown in FIG. 14, a user applies force against the sclera 603 with the scleral depressor head 101 while holding the handle 110 to form a scleral depression 604 that would allow visibility of internal structures of the eye 600 through the cornea 601 and the pupil 602. The emitted light 180 from the illuminated scleral depressor assembly 10 aids in visualization of the anatomy via transscleral illumination. Embodiments of illuminated scleral depressor assemblies described herein provide improvements over known devices by providing light emitted from the scleral depressor head approximately orthogonal to a center axis of the scleral depressor assembly.

Figure 15:
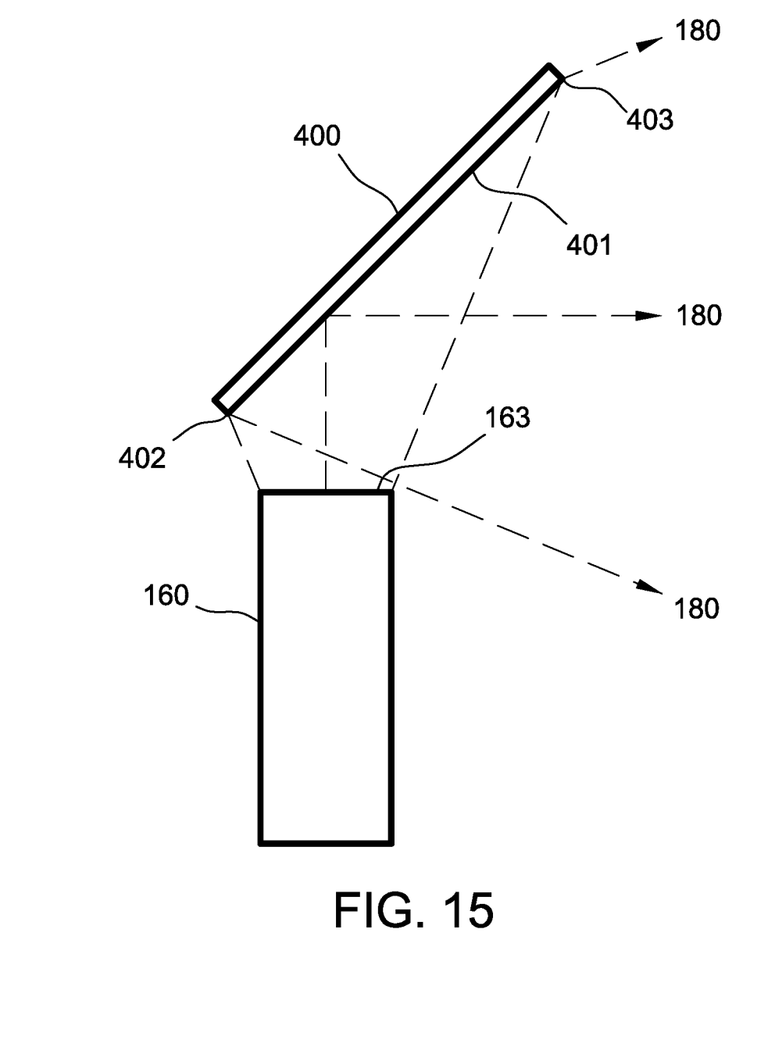
FIG. 15 is a schematic diagram of a comparative example.
Figure 16:
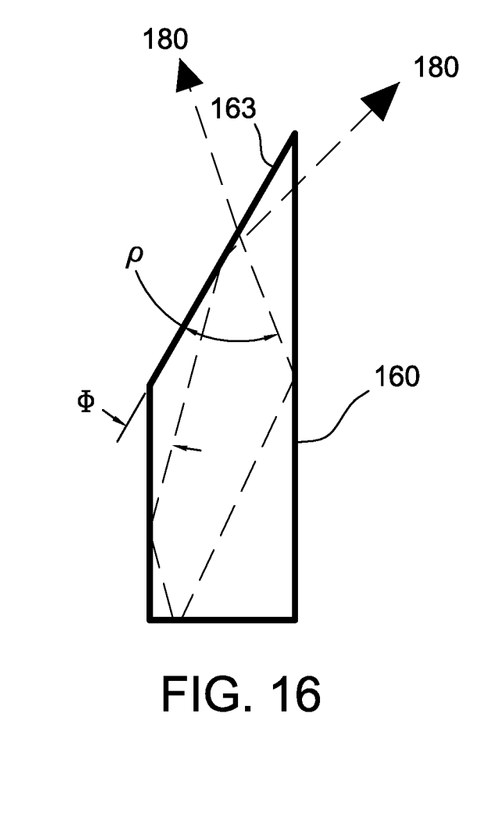
FIG. 16 is a schematic diagram of another comparative example.

FIGS. 15 and 16 illustrate diagrams of comparative embodiments of a flat fiber and angled reflector (FIG. 15) as well as a beveled fiber with no reflector (FIG. 16). The diagram of the flat fiber and angled reflector (FIG. 15) illustrates the effect on the diameter of the reflector 400 when the beveled end face 163 is not substantially adjacent to the entirety of the reflective surface 401 therefore increasing the diameter of the scleral depressor head 101 and limiting the user's access to the patient's eye. The diagram of the beveled fiber with no reflector (FIG. 16) illustrates the limitations of redirecting the emitted light 180 when relying solely on internal reflection. Light will reflect off the internal surface of the beveled end face 163 if the angle is lower than the critical angle, determined by the index of refraction, as seen by the ray with the internal angle of φ whereas the ray with the higher angle, ρ, does not reflect and therefore the angle of the emitted light 180 relative to the central axis 11 is limited.

Figure 17:
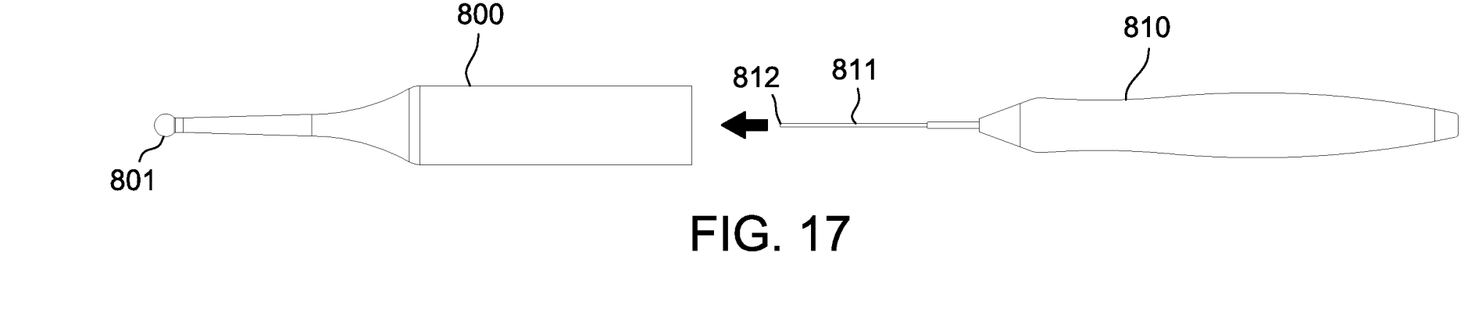
FIG. 17 is a side view of a comparative example of a known hollow scleral depressor that utilizes an endoilluminator to provide light for a transscleral illumination procedure.
Figure 18:
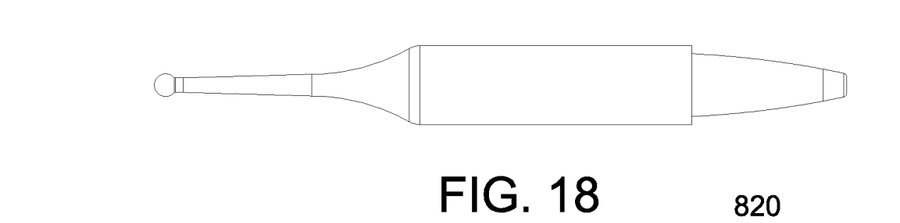
FIG. 18 is a side view of the comparative example of FIG. 17 in an assembled state.
Figure 19:
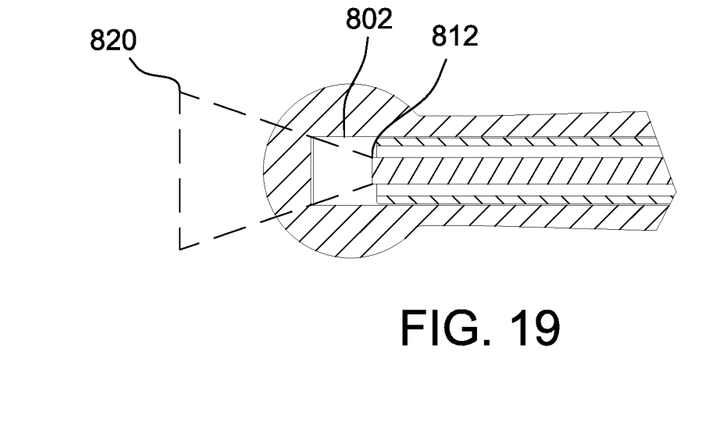
FIG. 19 is a cross-sectional view of a distal portion of the comparative example of FIG. 17.

FIGS. 17-19 illustrate another comparative example of a known hollow scleral depressor 800 that utilizes an endoilluminator 810 to provide light for a transscleral illumination procedure. In use, the endoilluminator shaft 811 is inserted into a hollow scleral depressor lumen 802 until the endoilluminator distal end 812 is positioned within the hollow scleral depressor transparent head 801 allowing the endoilluminator emitted light 820 to exit axially.

Exemplary embodiments of ophthalmic surgical instruments are described above in detail. The ophthalmic surgical instruments and their components are not limited to the specific embodiments described herein, but rather, components of the instruments may be utilized independently and separately from other components described herein. For example, the components may also be used in combination with other medical devices and systems, methods, and apparatuses, and are not limited to practice with only the systems and methods as described herein. Rather, the exemplary embodiments can be implemented and utilized in connection with many other applications.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

This written description uses examples to disclose the disclosure, including the best mode, and to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A scleral depressor assembly comprising:
 a scleral depressor comprising an elongate body and a head disposed at a distal end of the elongate body, wherein the scleral depressor defines an internal lumen extending through the elongate body and terminating within the head;
 an optical fiber disposed within the lumen and comprising a distal end positioned within the head, wherein the distal end comprises a beveled end face that is obliquely oriented with respect to a central axis of the internal lumen; and a reflector disposed at the distal end of the optical fiber and configured to reflect light emitted from the beveled end face along a light path out of the scleral depressor head in a direction that is approximately orthogonal to the central axis of the internal lumen.

2. The scleral depressor assembly of claim 1 further comprising a light source, wherein the optical fiber extends from a proximal end coupled to the light source to the distal end.

3. The scleral depressor assembly of claim 1, wherein the optical fiber is a first optical fiber extending from a planar proximal end to the beveled end face, wherein the scleral depressor lumen is adapted to receive a second optical fiber having a planar distal end that abuts with the proximal end of the first optical fiber to transmit light though the first and second optical fibers.

4. The scleral depressor assembly of claim 3, wherein the proximal end of the first optical fiber is disposed within the scleral depressor lumen.

5. The scleral depressor assembly of claim 4, wherein the proximal end of the first optical fiber is disposed within the head of the scleral depressor.

6. The scleral depressor assembly of claim 1, wherein the reflector comprises a reflective surface positioned on or adjacent the beveled end face of the optical fiber to reflect light emitted therethrough, wherein the reflective surface has a major dimension that is less than 3 times larger than a diameter of the optical fiber.

7. The scleral depressor assembly of claim 1, wherein the optical fiber has a diameter in the range of 0.25 millimeters (mm) to 1.0 mm.

8. The scleral depressor assembly of claim 1, wherein the optical fiber is constructed of polymethyl methacrylate or glass.

9. The scleral depressor assembly of claim 1, wherein the scleral depressor head is constructed of a transparent material.

10. The scleral depressor assembly of claim 9, wherein the scleral depressor head is constructed of acrylic, polycarbonate, glass, or combinations thereof.

11. The scleral depressor assembly of claim 1, wherein the reflector comprises a reflective surface comprising at least one of aluminum, silver, steel, or alloys thereof.

12. The scleral depressor assembly of claim 1, wherein the reflector comprises one of a deposition or a coating applied to the beveled end face of the optical fiber.

13. The scleral depressor assembly of claim 1, wherein the reflector comprises a disk that abuts the beveled end face of the optical fiber.

14. The scleral depressor assembly of claim 1, wherein the head is one of spherical or tear-drop shaped.

15. The scleral depressor assembly of claim 1, wherein the head comprises a concave engagement surface positioned within the light path traversed by light reflected by the reflector.

16. The scleral depressor assembly of claim 15, wherein the engagement surface is textured to increase friction between the scleral depressor head and a patient's tissue.

17. The scleral depressor assembly of claim 1, wherein the scleral depressor lumen contains an optically transparent fluid.

18. The scleral depressor assembly of claim 17, wherein the optically transparent fluid comprises saline.

19. The scleral depressor assembly of claim 1, wherein the optical fiber extends along a central longitudinal axis, and wherein the beveled end face is oriented at an oblique angle relative to the central longitudinal axis, wherein the oblique angle is in the range of 30° to 60°.

20. An illuminated scleral depressor assembly comprising:

a scleral depressor comprising an elongate body and a head disposed at a distal end of the elongate body, wherein the scleral depressor defines an internal lumen extending through the elongate body and terminating within the head;

a light source;

an optical fiber disposed within the lumen and extending between the light source and the scleral depressor, wherein the optical fiber comprises a distal end positioned within the head, and wherein the distal end comprises a beveled end face that is obliquely oriented with respect to a central axis of the internal lumen; and a reflector disposed at the distal end of the optical fiber and configured to reflect light emitted from the beveled end face along a light path out of the scleral depressor head in a direction that is approximately orthogonal to the central axis of the internal lumen.

21. A method of assembling a scleral depressor assembly, the method comprising:

providing a scleral depressor including an elongate body and a head disposed at a distal end of the elongate body, wherein the scleral depressor defines an internal lumen extending through the elongate body and terminating within the head;

providing an optical fiber disposed within the lumen and including a distal end positioned within the head, wherein the distal end comprises a beveled end face that is obliquely oriented with respect to a central axis of the internal lumen;

providing a reflector disposed at the distal end of the optical fiber; and coupling the optical fiber to a light source such that light emitted by the light source is transmitted through the optical fiber and the reflector reflects light emitted from the beveled end face along a light path out of the scleral depressor head in a direction that is approximately orthogonal to the central axis of the internal lumen.

* * * * *